United States Patent [19]

Debat et al.

[11] 4,254,112

[45] Mar. 3, 1981

[54] INULA EXTRACT, ITS METHOD OF PREPARATION AND ITS USE AS PHARMACEUTICAL

[75] Inventors: Jacques Debat, Saint Cloud; Jean Lemoine, Garches; Françoise Lier née Gabillault, Plaisir, all of France

[73] Assignee: Laboratoire Debat, Paris, France

[21] Appl. No.: 42,155

[22] Filed: May 24, 1979

[30] Foreign Application Priority Data

May 31, 1978 [GB] United Kingdom .............. 25615/78

[51] Int. Cl.³ .......................... A01N 9/02; A01N 9/08
[52] U.S. Cl. .................................................... 424/195
[58] Field of Search ........................................ 424/195

[56] References Cited

PUBLICATIONS

Caldes et al., "Planta Medica", 27 (1975), pp. 72-76.

*Primary Examiner*—Elbert L. Roberts
*Attorney, Agent, or Firm*—Bacon & Thomas

[57] ABSTRACT

This invention relates to the preparation of an extract of *Inula* and related species such as *Inula Viscosa* and *Inula graveolens* (which belong to the family *compositae*) which is useful in therapy, in particular as bacteriostatic and fungistatic agent.

This extract is useful in the treatment of human beings suffering from infectious diseases.

6 Claims, No Drawings

INULA EXTRACT, ITS METHOD OF PREPARATION AND ITS USE AS PHARMACEUTICAL

BACKGROUND OF THE INVENTION AND PRIOR ART

Species of *Inula* are well known plants of the family *compositae* which have been described by G. GARNIER in "Ressources Medicinales de la Flore Francaise" vol. 2, page 1358 (Vigot Freres ed., Paris, 1961). Chemical components of several *Inula* species have been disclosed in Phytochemistry 17, 1165 (1978).

*Inula viscosa* and *Inula graveolens* which grow in the Mediterranean basin are so similar that they can be distinguished only when they are flowering.

It has been disclosed by G. CALDES et al., in Planta Medica 27, 72–76 (1975) that extracts of *Inula graveolens* (obtained by extraction with hot and respectively cold water and lyophilization) tested as antibacterial agents against *Staphylococcus aureus* and *Streptococcus faecium* and as antimalarial agents against *Plasmodium berghei*, are inactive.

SUBJECT OF THE INVENTION

The subject of the invention is to propose a new method of extraction of *Inula* in order to obtain an extract which is useful in the treatment of infectious diseases as bacteriostatic and fungistatic agent.

DETAILED DESCRIPTION OF THE INVENTION

According to the present invention, the entire plant (that is to say the stems, the leaves, the floral apices, the fruit and the roots) or a part of the plant, is extracted with at least one solvent. The product thus obtained is then purified, if necessary, and recovered according to a method known per se, The extraction can be carried out by using, per liter of solvent, 30 to 150 g of ground dry plant. Solvent which can be used include alcohols (such as methanol, ethanol, propanol and isopropanol), ketones (such as acetone, methyl ethyl ketone and methyl propyl ketone), ethers (such as dimethyl ether, diethyl ether and diisopropyl ether), esters (such as ethyl acetate), hydrocarbons (such as pentane, hexane, cyclopentane, cyclohexane, petroleum ether and benzene), halogenated hydrocarbons (such as chloroform and methylene chloride), and mixtures thereof.

The best mode for carrying out the invention consists in extracting an *Inula* species selected from the group comprising *Inula viscosa* and *Inula graveolens*, with a solvent selected from the group comprising diethyl ether, ethyl acetate, ethanol and chloroform, the preferred solvents being diethyl ether, ethyl acetate and ethanol. Preferably the extraction is carried out on the entire plant ground and dried (in an oven at 37° C.).

The following examples illustrate the invention.

EXAMPLE 1

Total extract of *Inula viscosa*

200 g of the whole plant of *Inula viscosa* are dried in an oven at 37° C., ground, and extracted with 3 l. of ethanol in a Soxhlet apparatus for 4 hours. The insoluble material is discarded and the ethanol solution, after drying over anhydrous sodium sulphate, is evaporated to dryness under reduced pressure. 8 g of a soft extract are obtained (yield 4% by weight with respect to the starting plant material).

EXAMPLE 2

Total extract of *Inula viscosa*

By using chloroform instead of ethanol the material disclosed in Example 1 gives 8 g of a soft extract.

EXAMPLE 3

Total extract of *Inula viscosa*

200 g of the whole plant of *Inula viscosa* are dried in an oven at 37° C., ground, and extracted with 3 l. of diethyl ether at 5° to 12° C. for 48 hours. The insoluble material is discarded and the diethyl ether solution is evaporated to dryness under reduced pressure. 6.3 g of a soft extract (which is coded as C.94) are obtained. Yield = 3.1% by weight with respect to the starting plant material.

The extracts of Examples 1 to 3 give, by thin layer chromatography the very same three spots, under the following operating conditions:

| | |
|---|---|
| support | silica; |
| mobile phase | hexane - chloroform - methanol (3:9:1 v/v/v); |
| developer | sulphuric acid - vanillin (1 g of vanillin per 100 ml of concentrated $H_2SO_4$ of density 1.84); |

EXAMPLES 4 TO 6

Total extracts of *Inula graveolens*

By treating 200 g of the whole plant of *Inula graveolens* which have been dried in an oven at 37° C. and ground, according to the methods described in Examples 1 to 3, three soft extracts of *Inula graveolens* are respectively obtained with the same yields.

EXAMPLE 7

Total extract of *Inula viscosa*

400 g of the whole plant of *Inula viscosa* are dried at 37° C. in an oven, ground, and extracted with 3 l. of diethyl ether in a Soxhlet apparatus. The insoluble material is discarded and the diethyl ether solution, after drying over anhydrous sodium sulphate is evaporated to dryness under reduced pressure. 7 g of a total extract are obtained (yield: 1.75% by weight with respect to the starting plant material).

EXAMPLE 8

The total extract of example 7 subjected to a column chromatography [the column being filled with silica ("Kieselgel 60" manufactured by Merck and Co.)], gives four fractions (F1-F4) as indicated in Table I.

TABLE I

| Eluent | Fraction | Yield[a] |
|---|---|---|
| Hexane-methylene chloride (50:50 v/v) | F1 | 0.25% |
| Hexane-methylene chloride (50:50 v/v)[b] | F2 | 0.10% |
| methylene chloride | F3 | 0.10% |
| methylene chloride-methanol (99:1 v/v) | F4 | 0.12% |

Notes:
[a] by weight with respect to the plant.
[b] F2 requires a longer period of time then F1 to be eluated.

The extracts of examples 1–7 according to the invention exhibit bacteriostatic activity against gram (+) and gram (−) bacteria and a fungistatic activity against fungi. In particular the extract of Example 3 exhibits the MIC values given in Table II.

TABLE II

| Microorganism | MIC (μg/ml) |
|---|---|
| *Staphylococcus aureus* London | 1 |
| *Escherichia coli* | 33 |
| Proteus | 33 |
| *Aspergillus niger* | 3 |

The invention includes within its scope a therapeutic composition comprising, in association with a physiologically acceptable excipient, a pharmaceutically effective amount of an extract of the invention. Such a composition can be administered orally, locally or by injection.

What is claimed is:

1. A method of preparation of an extract of an *Inula* species selected from the group consisting of *Inula viscosa* and *Inula graveolens* useful in therapy which comprises extracting the entire plant or a part of said plant, with an organical solvent selected from the group consisting of alcohols, ketones, ethers, hydrocarbons, halogenated hydrocarbons and mixtures thereof.

2. A method of preparation of an extract of *Inula* useful in therapy as bacteriostatic and fungistatic agent which comprises the extraction of an *Inula* species selected from the group consisting of *Inula viscosa* and *Inula graveolens* with an organical solvent selected from the group consisting of alcohols, ketones, ethers, hydrocarbons, halogenated hydrocarbons and mixtures thereof, 1 l of organical solvent being used for 30 to 150 g of plant.

3. A method according to claim 2 which comprises extracting 30 to 150 g of ground dried entire plant with 1 l of an organical solvent selected from the group consisting of ethanol, ethyl acetate, diethyl ether and chloroform, and evaporating the solution thus obtained under reduced pressure to dryness.

4. A method according to claim 2 which comprises extracting 30 to 150 g of a ground dried part of the plant selected from stems, leaves, floral apices, fruit and roots, with 1 l of an organical solvent selected from the group consisting of ethanol, ethyl acetate, diethyl ether and chloroform, and evaporating the solution thus obtained under reduced pressure to dryness.

5. An extract of *Inula* obtained from a species selected from *Inula viscosa* and *Inula graveolens* according to the method of claim 3.

6. A therapeutical composition useful in the treatment of human beings suffering from infectious diseases comprising in association with a physiologically acceptable excipient, a pharmaceutically effective amount of an *Inula* extract according to claim 5.

* * * * *